(12) United States Patent
Gao et al.

(10) Patent No.: US 8,711,349 B2
(45) Date of Patent: Apr. 29, 2014

(54) HIGH THROUGHPUT THIN FILM CHARACTERIZATION AND DEFECT DETECTION

(71) Applicant: KLA-Tencor Corporation, Milpitas, CA (US)

(72) Inventors: Xiang Gao, San Jose, CA (US); Philip D. Flanner, III, Union City, CA (US); Leonid Poslavsky, Belmont, CA (US); Zhiming Jiang, Pleasanton, CA (US); Jun-Jie Ye, Shanghai (CN); Torsten Kaack, Los Altos, CA (US); Qiang Zhao, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/626,023

(22) Filed: Sep. 25, 2012

(65) Prior Publication Data

US 2013/0083320 A1    Apr. 4, 2013

Related U.S. Application Data

(60) Provisional application No. 61/539,748, filed on Sep. 27, 2011, provisional application No. 61/644,137, filed on May 8, 2012.

(51) Int. Cl.
   *G01N 21/95* (2006.01)
(52) U.S. Cl.
   USPC .................................. 356/237.5; 356/237.4
(58) Field of Classification Search
   USPC ........................................ 356/327.1–237.5
   See application file for complete search history.

(56) References Cited

U.S. PATENT DOCUMENTS

| | | | | |
|---|---|---|---|---|
| 5,920,067 | A * | 7/1999 | Cresswell et al. | 850/20 |
| 6,014,209 | A * | 1/2000 | Bishop | 356/237.5 |
| 6,072,568 | A * | 6/2000 | Paton et al. | 356/32 |
| 6,259,521 | B1 * | 7/2001 | Miller et al. | 356/237.5 |
| 6,327,035 | B1 * | 12/2001 | Li et al. | 356/432 |
| 6,459,482 | B1 * | 10/2002 | Singh et al. | 356/243.1 |
| 6,465,265 | B2 | 10/2002 | Opsal et al. | |
| 6,650,423 | B1 * | 11/2003 | Markle et al. | 356/601 |

(Continued)

OTHER PUBLICATIONS

He, G., et al., "Thickness-modulated Optical Dielectric Constants and Band Alignments of HfOxNy Gate Dielectrics," Journal of Applied Physics, Jan. 14, 2009, 105, 014109, pp. 1-4, USA.

(Continued)

*Primary Examiner* — Sang Nguyen
(74) *Attorney, Agent, or Firm* — Spano Law Group; Joseph S. Spano

(57) ABSTRACT

Methods and systems for determining band structure characteristics of high-k dielectric films deposited over a substrate based on spectral response data are presented. High throughput spectrometers are utilized to quickly measure semiconductor wafers early in the manufacturing process. Optical dispersion metrics are determined based on the spectral data. Band structure characteristics such as band gap, band edge, and defects are determined based on optical dispersion metric values. In some embodiments a band structure characteristic is determined by curve fitting and interpolation of dispersion metric values. In some other embodiments, band structure characteristics are determined by regression of a selected dispersion model. In some examples, band structure characteristics indicative of band broadening of high-k dielectric films are also determined. The electrical performance of finished wafers is estimated based on the band structure characteristics identified early in the manufacturing process.

21 Claims, 5 Drawing Sheets

(56) References Cited

U.S. PATENT DOCUMENTS

| | | |
|---|---|---|
| 7,239,391 B2 | 7/2007 | Synowicki et al. |
| 7,414,721 B1 | 8/2008 | Suvkhanov et al. |
| 2010/0068834 A1 | 3/2010 | Hachigo et al. |

OTHER PUBLICATIONS

Price, J., et al., "Identification of Interfacial Defects in High-k Gate Stack Films by Spectroscopic Ellipsometry," Journal of Vacuum Science and Technology, American Vacuum Society, Feb. 9, 2009, B 27(1), pp. 310-312, USA.

Price, J., et al., "Identification of Sub-Band-Gap Absorption Features at the HfO2/Si(100) Interface via Spectroscopic Ellipsometry," Applied Physics Letters, American Institute of Physics, Aug. 10, 2007, 91, 061925, pp. 1-3, USA.

International Search Report and Written Opinion mailed on Mar. 6, 2013, for PCT Application No. PCT/US2012/057019 filed on Sep. 25, 2012, by KLA-Tencor Corporation, 6 pages.

* cited by examiner

HIGH THROUGHPUT THIN FILM CHARACTERIZATION AND DEFECT DETECTION

CROSS REFERENCE TO RELATED APPLICATION

The present application for patent claims priority under 35 U.S.C. §119 from U.S. provisional patent application Ser. No. 61/644,137, entitled "Band Gap and Defect Measurement and Monitoring for Semiconductor Manufacturing," filed May 8, 2012, and from U.S. provisional patent application Ser. No. 61/539,748, entitled "Monitoring Dielectric Constant and Energy Band Gap of Material in Semiconductor Manufacturing," filed Sep. 27, 2011. The subject matter of each of the aforementioned U.S. provisional patent applications is incorporated herein by reference.

TECHNICAL FIELD

The described embodiments relate to systems for wafer inspection, and more particularly to characterization and defect detection of thin films used in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

Semiconductor devices are increasingly valued based on their energy efficiency, rather than speed alone. For example, energy efficient consumer products are more valuable because they operate at lower temperatures and for longer periods of time on a fixed battery power supply. In another example, energy efficient data servers are in demand to reduce their operating costs. As a result, there is a strong interest to reduce the energy consumption of semiconductor devices.

Leakage current through insulator layers is a major energy loss mechanism of semiconductor devices manufactured at the 65 nm technology node and below. In response, electronic designers and manufacturers are adopting new materials (e.g., hafnium silicate (HfSiO4), nitrided hafnium silicates (HfSiON), hafnium dioxide (HfO2), zirconium silicate (ZrSiO4), etc.) with higher dielectric constants and lower extinction coefficients than traditional materials (e.g., silicon dioxide). These "high-k" materials reduce leakage current and enable the manufacture of smaller sized transistors.

Along with the adoption of new dielectric materials, the need has arisen for measurement tools to characterize the dielectric properties and band structures of high-k materials early in the manufacturing process. More specifically, high throughput monitoring tools are required to monitor and control the deposition of high-k materials during wafer manufacture to ensure a high yield of finished wafers. Early detection of deposition problems is important because the deposition of high-k materials is an early process step of a lengthy and expensive manufacturing process. In some examples, a high-k material is deposited on a wafer at the beginning of a manufacturing process that takes over one month to complete.

Measurements of the material composition of high-k dielectric layers have been used as indicators for process monitoring. For high-k materials such as SiHfON, it was found that differing percentages of nitrogen and hafnium, different deposition temperatures and deposition cycle times, different intermediate layers, etc., produce different dispersion values and different energy band structures. This affects chip performance at the end of the manufacturing process. In some examples, an X-ray spectrometer has been utilized to accurately measure the material composition of high-k dielectric layers. However, X-ray spectroscopy suffers from high cost and low throughput, making it undesireable for use as a high throughput production monitoring tool. In some other examples, dispersion properties of the high-k dielectric layer (e.g., refractive index, n, and extinction coefficient, k) have been used to calculate material composition based on empirical models. This approach has the advantage of lower cost and higher throughput relative to X-ray spectroscopic techniques. One such example is presented in U.S. patent application Ser. No. 13/524,053 assigned to KLA-Tencor Technologies, Corp.

Although the material composition of a high-k material layer is a strong indicator of deposition process parameters, it does not directly correlate with end of line electrical properties, such as leakage current, etc. For example, in the case of SiHfON, a shift of deposition rate and temperature may produce a film with differing structural defects or different band structure while material composition remains unchanged. The resulting structural defects or band structure may adversely increase leakage current, despite the fact that the material composition has not changed. Similarly, a process that produces a different material composition may also result in reduced structural defects and a more favorable band structure. In this case, monitoring based on material composition may result in a false negative result where fault is found based on material composition when in fact the material structure and properties results in reduced leakage current.

Accordingly, it would be advantageous to develop high throughput methods and/or systems for characterizing high-k dielectric layers early in the manufacturing process to identify whether resulting finished wafers will have satisfactory electrical properties.

SUMMARY

Methods and systems for determining band structure characteristics of high-k dielectric films deposited over a substrate based on spectral response data are presented. The electrical performance of finished wafers is estimated based on the band structure characteristics identified early in the manufacturing process.

High throughput spectrometers such as ellipsometers or reflectometers quickly measure semiconductor wafers early in the manufacturing process. In addition, these optical tools are capable of gathering useful characterization data of high-k dielectric films at spectral energy values below five electron volts. This enables the identification of defects visible only in this spectral energy range.

Optical dispersion metrics are determined based on the spectral data. In some examples, the spectral response data is processed to determine film thickness and dispersion metrics (e.g., n and k) from an analytical dispersion model (e.g., Lorentzian models). In some other examples, spectral response data is processed to determine film thickness and dispersion metrics (e.g., n and k) from an empirical dispersion model where the dispersion metric is calculated numerically. Many other dispersion metrics may be contemplated. For example, any of the real ($\in_1$) and imaginary ($\in_2$) components of the complex dielectric constant, skin depth, absorption constant, attenuation constant, or others may be determined based on the spectral data.

Band structure characteristics such as band gap, band edge, and defects are determined based on optical dispersion metric values. In some examples, band structure characteristics are determined by regression of a selected dispersion model. In some other examples, an interpolated band gap of a high-k dielectric layer is determined by curve fitting and interpolation of an optical dispersion metric over a focused spectral range. In some examples, a band edge of a high-k dielectric layer is determined when an optical dispersion metric exceeds a threshold value. In some examples, band broadening associated with a high-k dielectric layer is determined based on the difference between the band edge and the interpolated band gap.

In some other examples, defects are determined based on optical dispersion metric values. For example, a defect may be identified when an optical dispersion metric exceeds a threshold value. In another example, a defect may be identified when the full width, half maximum (FWHM) value of the dispersion metric exceeds a threshold value. In another example, the area under a locus of dispersion metric values may be used to identify a defect.

In another aspect, the methods and systems presented herein may be applied to multiple layers characterized by the same spectral data set.

The foregoing is a summary and thus contains, by necessity, simplifications, generalizations, and omissions of detail. Consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
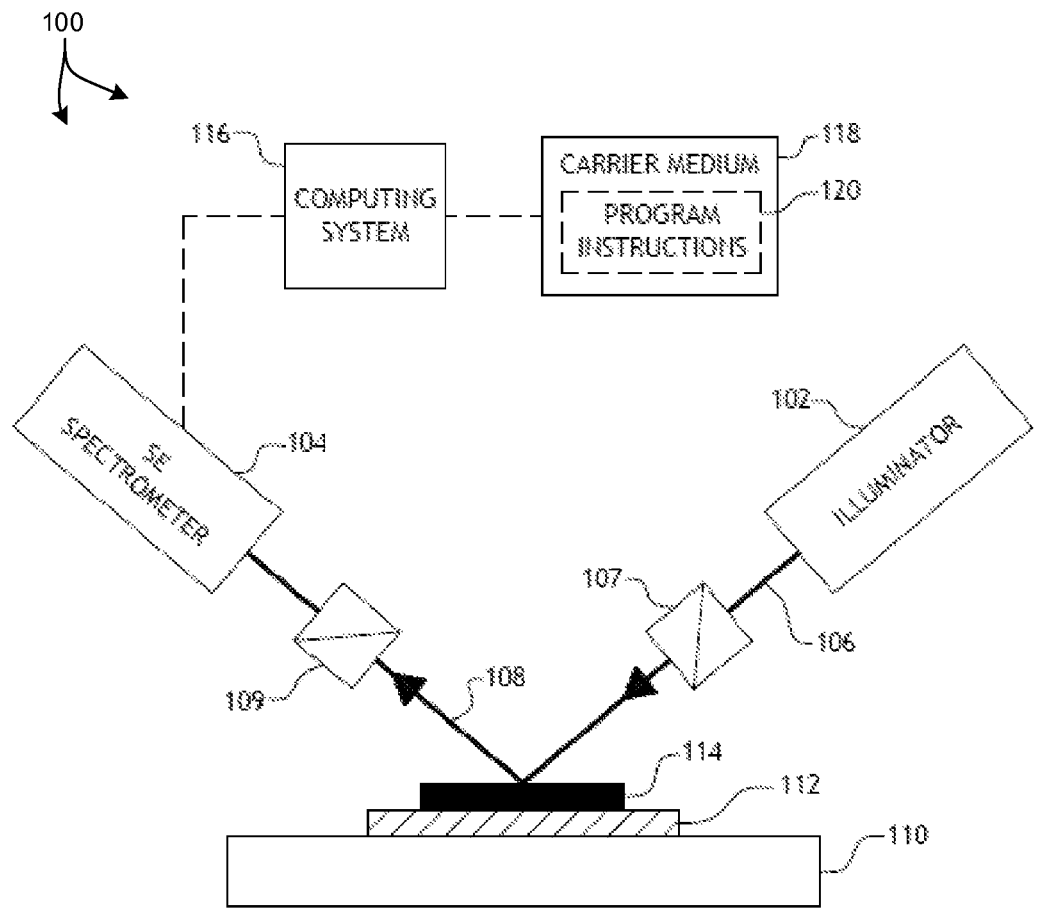
FIG. 1 is a simplified diagram illustrative of a wafer inspection system 100 including thin film characterization functionality.

FIG. 1 illustrates a system 100 for measuring a band structure characteristic of a thin film of a semiconductor wafer, in accordance with one embodiment of the present invention. As shown in FIG. 1, the system 100 may be used to perform spectroscopic ellipsometry on one or more films 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of the thin film 114.

In a further embodiment, the system 100 may include one or more computing systems 116. The one or more computing systems 116 may be communicatively coupled to the spectrometer 104. In one aspect, the one or more computing systems 116 may be configured to receive a set of spectral measurements performed by the spectrometer 104 on one or more wafers. Upon receiving results of the one or more sampling process from the spectrometer, the one or more computing systems 116 may then calculate an optical dispersion metric. In this regard, the computing system 116 may extract the real component (n) and the imaginary component (k) of the complex index of refraction of the thin film across the selected spectral range (e.g., 150-850 nm) for the acquired spectrum from the spectrometer 104. Further, the computing system 116 may extract the n- and k-curves utilizing a regression process (e.g., ordinary least squares regression) applied to a selected dispersion model. In a preferred embodiment, the selected dispersion model may include a sum model with two Tauc Lorentz components (Sum-TL model). In additional embodiments, the selected dispersion model may include a harmonic oscillator model.

Figure 3A:
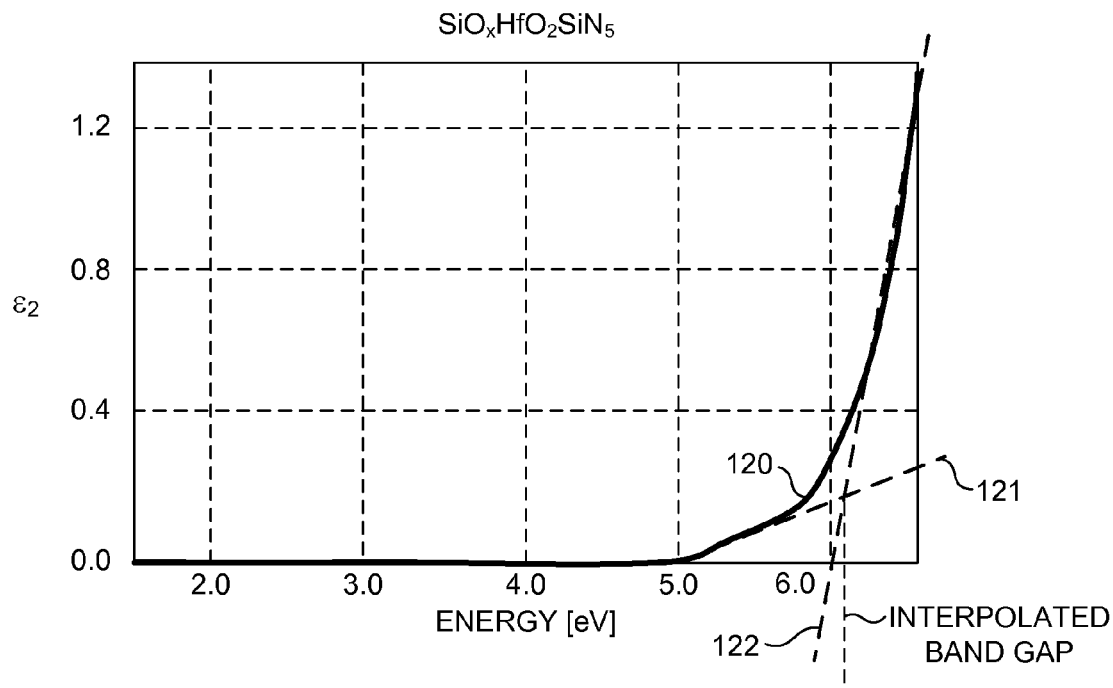
FIGS. 3A-3B illustrate an optical dispersion curve associated with a thin film material layer and band structure characteristics derived from the curve.
Figure 3B:
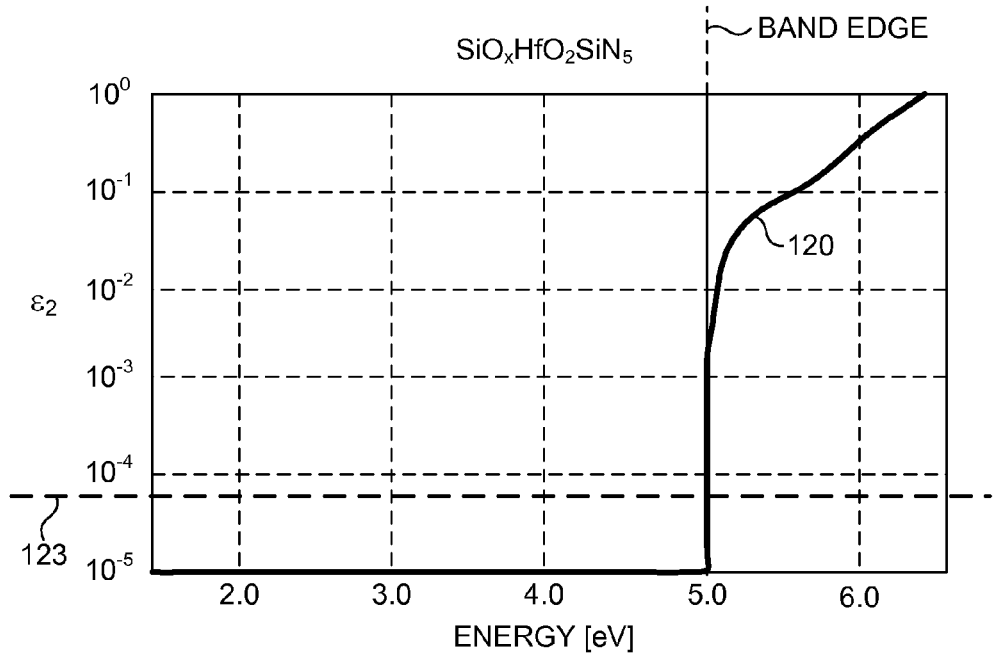
Figure 4:
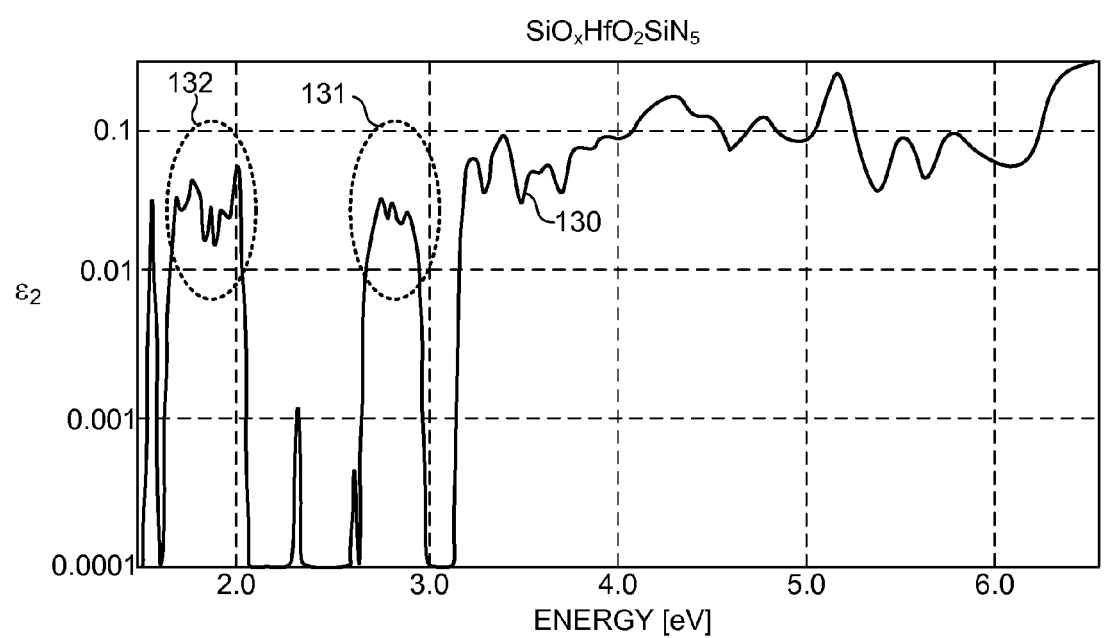
FIG. 4 is a plot illustrative of an optical dispersion curve associated with a thin film material layer and band structure defects identified from the curve.

In a further embodiment, the computing system 116 may determine a band structure characteristic indicative of an electrical performance of the film 114 based on the optical dispersion metric. For example, the computing system 116 may be configured to automatically identify trends within an optical dispersion curve (e.g., FIGS. 3A-3B and FIG. 4) that is representative of the value of the optical dispersion metric over the selected spectral range. For instance, the computing system 116 may identify energy band defects observable in an optical dispersion curve. In another example, the computing system 116 may identify the material band gap observable in an optical dispersion curve. In some examples, the computing system 116 may be configured to identify trends within an optical dispersion curve using the aid of user input. For instance, an optical dispersion curve may be presented to a user on a display (not shown), such as a liquid crystal display. The user may then identify trends in an optical dispersion curve by entering information into the computing system 116 using a user interface device (e.g., mouse, keyboard, trackpad, trackball, touch screen, or the like). In this regard, the user may select, or "tag," portions of the optical dispersion curves pertinent to analysis, with which the computing system may then, in turn, perform further or refined analysis. Applicant notes that specifics related to the analysis of optical dispersion curves, as shown in FIGS. 3A-3B and FIG. 4 will be discussed in greater detail further herein.

Figure 2:
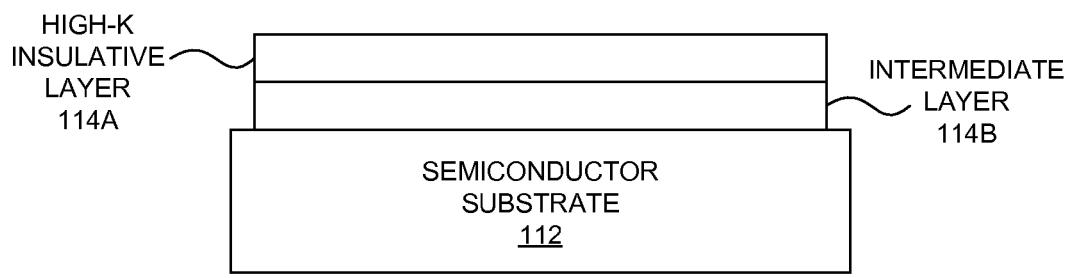
FIG. 2 is a simplified diagram illustrative of a semiconductor substrate 112 with attached thin film layers 114A and 114B that may be characterized by methods and systems as described herein.

As illustrated in FIG. 2, in some embodiments, an intermediate layer 114B is located between a semiconductor substrate 112 (e.g., silicon) and a high-k insulative layer 114A to promote adhesion between the high-k material and the semiconductor substrate. Typically, the intermediate layer 114B is very thin (e.g., ten Angstroms). In some examples, the high-k insulative layer 114A and the intermediate layer 114B are modeled together as one layer for purposes of analysis employing the methods and systems as described herein. In this example, the one or more computing systems 116 may determine a band structure characteristic indicative of an electrical performance of the film layer 114 including both the intermediate layer 114B and high-k insulative layer 114A based on an optical dispersion metric associated with the aggregate film layer 114. However, in some other examples, each layer may be modeled separately. In this example, the one or more computing systems 116 may determine a band structure characteristic indicative of an electrical performance of the high-k insulative layer 114A and a band structure characteristic indicative of an electrical performance of the intermediate layer 114B film layer based on optical dispersion metrics associated with each physically distinct layer, respectively.

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100.

Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Band structure characteristics (e.g., band gap, band edge, energy band defects, interface defects, band broadening, etc.) are major contributors to unintended leakage current through high-k material layers of finished wafers. Hence, band structure characteristics of material layers of unfinished wafers are suitable indicators of the electrical performance of finished wafers. In one aspect, band structure characteristics are derived from data obtained from high throughput, optically based, thin film measurement tools. The resulting band structure characteristics are used to predict electrical performance of finished wafers at an early point in the manufacturing process.

Figure 5:
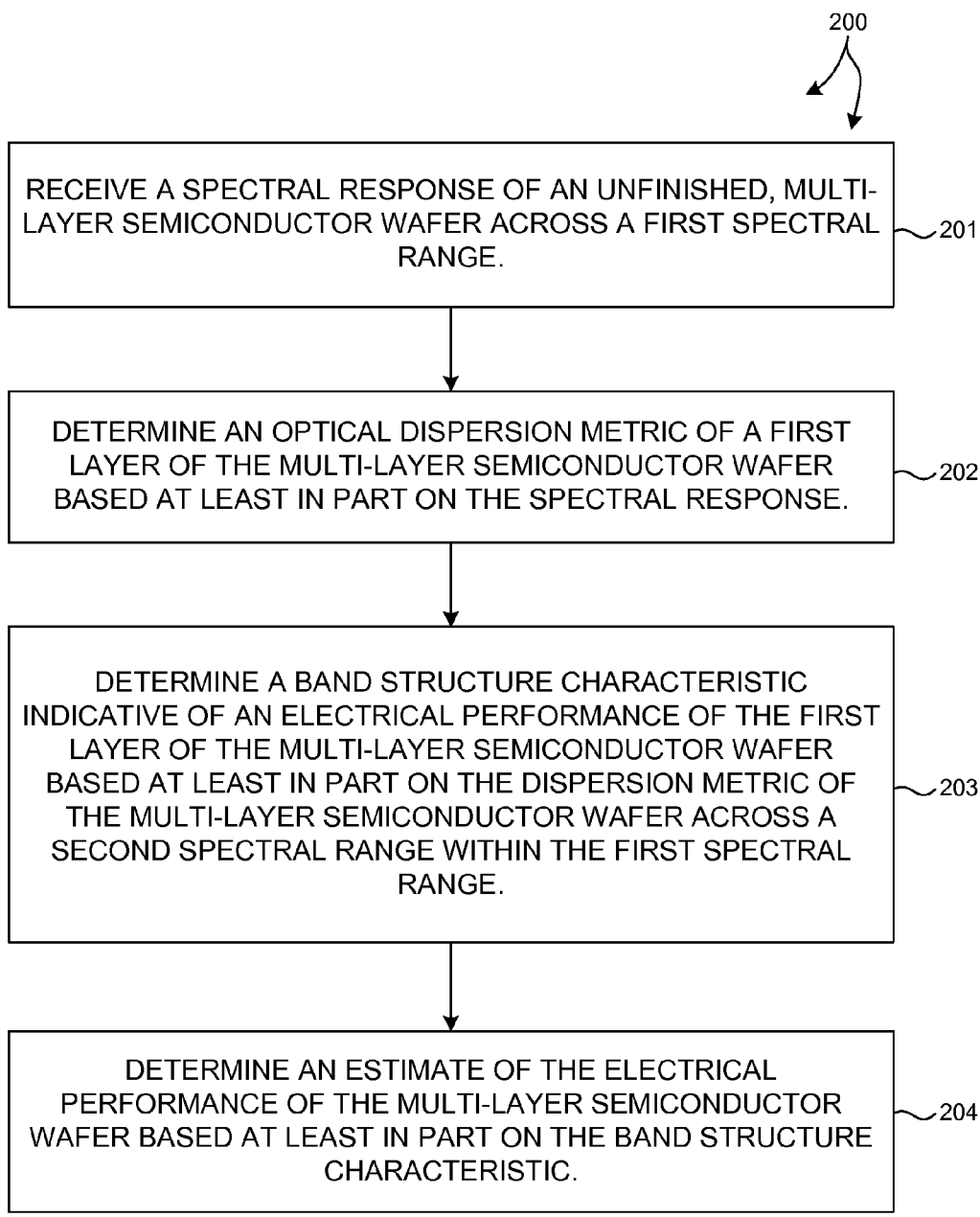
FIG. 5 is a flowchart 190 illustrative of a method 200 of determining band structure characteristics from spectral response data.

FIG. 5 illustrates a process flow 200 suitable for implementation by the system 100 of the present invention. In one aspect, it is recognized that data processing steps of the process flow 200 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In step 201, a spectral response of an unfinished, multi-layer semiconductor wafer across a broad spectral range is received after a high-k thin film is deposited on the wafer. For example, spectra may be received from an ellipsometer 101. In another example, spectra may be received from a reflectometer (not shown). The spectral data may be acquired from each of the thin films 114 deposited on the wafer 112 utilizing the spectroscopic ellipsometer 101. For instance, the ellipsometer 101 may include an illuminator 102 and a spectrometer 104, as discussed previously herein. The spectrometer 104 may transmit results associated with a spectroscopic measurement of the thin films of the wafer to one or more computing systems 116 for analysis. In another example, the spectra for multiple thin films 114 may be acquired by importing previously obtained spectral data. In this regard, there is no requirement that the spectral acquisition and the subsequent analysis of the spectral data need be contemporaneous or performed in spatial proximity. For instance, spectral data may be stored in memory for analysis at a later time. In another instance, spectral results may be obtained and transmitted to analysis computing system located at a remote location.

In step 202, an optical dispersion metric associated with a layer of the semiconductor wafer is determined based on the spectral response of the unfinished, multi-layer wafer. Many useful optical dispersion metrics may be contemplated. For example, any of the real (n) and imaginary (k) components of the complex index of refraction may be determined based on the spectral data. In another example, any of the real ($\in_1$) and imaginary ($\in_2$) components of the complex dielectric constant may be determined based on the spectral data. In other examples, any of the square root of $\in_2$, absorption constant $\alpha = 4\pi k/\lambda$, conductivity ($\sigma$), skin depth ($\delta$), and attenuation constant $(\sigma/2)*\mathrm{sqrt}(\mu/\in)$ may be determined based on the spectral data. In other examples, any combination of the aforementioned optical dispersion metrics may be determined based on the spectral data. The aforementioned optical dispersion metrics are provided by way of non-limiting example. Other optical dispersion metrics or combinations of metrics may be contemplated.

In some examples, the spectral response data is processed to determine film thickness and dispersion metrics (e.g., n and k) from an analytical dispersion model (e.g., Lorentzian models). In some other examples, spectral response data is processed to determine film thickness and dispersion metrics (e.g., n and k) from an empirical dispersion model where the dispersion metric is calculated numerically.

In one example, Off-Line Spectral Analysis (OLSA) software available from KLA-Tencor Corporation (Milpitas, Calif.) is used to numerically calculate any of k, $\in_2$, $\sigma$ and other user-defined metrics without exact knowledge of the dispersion property of a material. In a preferred example, $\in_2$, is calculated using OLSA based on spectral data taken by an ellipsometer from a wafer 112 including a thin film layer 114A of $SiO_x HfO_2 SiN_5$ material. The locus of values 120 of $\in_2$ is illustrative of dispersion metric, $\in_2$, over a measured spectral range. FIG. 3B illustrates the same locus of values 120 plotted in logarithmic format.

In some examples, the optical dispersion metric may be generated by extracting the real component (n) and the imaginary component (k) of the complex index of refraction across the selected spectral range for the acquired spectrum utilizing a regression process applied to a selected dispersion model. In this regard, a regression method may be applied to the measured spectral data using a selected dispersion model. In one embodiment, a sum model with two Tauc-Lorentz components may be utilized to generate the n- and k-dispersion curves for each of the thin films of the wafers. In another embodiment, a single component Tauc-Lorentz may be utilized to generate the n- and k-dispersion curves for each of the thin films of the wafers. In another embodiment, a Cody-Lorentz model may be utilized to generate the n- and k-dispersion curves for each of the thin films of the wafers. In yet another embodiment, a harmonic oscillator model may be utilized to generate the n- and k-dispersion curves for each of the thin films of the wafers.

In step 203, a band structure characteristic indicative of an electrical performance of the layer is determined based at least in part on the optical dispersion metric across a subset of the original spectral range. Typically, limiting the spectral range for identification of a band structure characteristic is preferred because dispersion model results are generally more accurate over smaller spectral ranges. Thus, it may be advantageous to identify dispersion metric values from spectral data over a broad range initially to identify areas where more detailed analysis should be focused (e.g., near the band gap of the material). Based on this knowledge, the dispersion models may be recalculated based on a smaller range of spectral data. Based on the energy region of interest, a band structure characteristic is determined.

In some examples, the band structure characteristic is determined directly from dispersion models applied to the particular film layer. For example, an analytical model, empirical model, or a combination of both analytical and empirical models includes a model of dispersion with a band structure characteristic (e.g., band gap) as a parameter. In this manner the band structure characteristic is determined directly through regression of the dispersion model (i.e., the model solution itself determines the band structure characteristic).

In some examples, the band structure characteristic is determined by analysis of the values of an optical dispersion metric (e.g., k, $\in 2$ or other parameters that describe the absorption or extinction of electromagnetic energy by the high-k material) over a spectral range.

In one example, a band structure characteristic is a band edge value determined from an optical dispersion metric. As illustrated in FIG. 3B, a band edge value is defined when $\in_2$ exceeds a threshold value 123. In the illustrated example, a band edge value of the measured film is five electron volts.

In another example, a band structure characteristic is an interpolated band gap value determined by curve fitting and interpolation of an optical dispersion metric. For example, as illustrated in FIG. 3A, an interpolated band gap is determined based on curve fitting and interpolation of $\in_2$. In general, the amorphous structure of a high-k material, layer interfaces, and misaligned energy bands contribute to the broadening of the absorption edges at lower energy levels. Curve fitting methods are used to determine an interpolated band gap that significantly reduces the impact of broadening effects in the determination of band gap. For example, as illustrated in FIG. 3A, line 121 is representative of a linear fit to values of $\in_2$ between five electron volts and 5.5 electron volts. Line 122 is representative of a linear fit to values of $\in_2$ between 6.2 electron volts and 6.7 electron volts. Their intersection at approximately six electron volts is the interpolated band gap value. Although, as illustrated, lines 121 and 122 are linear fits to values of $\in_2$ over different spectral regions, other fitting methods may be employed. For example, higher order polynomial functions, exponential functions, or other mathematical functions may be used to fit optical dispersion values over different spectral regions to obtain an estimate of band gap of the measured film layer.

As illustrated in FIGS. 3A-3B, the interpolated band gap that discounts broadening effects and the band edge value that includes broadening effects are different values. The difference between the interpolated band gap and the band edge can be used as a band structure characteristic indicative of the magnitude of broadening effects present in the measured film. In this manner, process improvements can be separately judged based on their impact on broadening effects and on band gap absent broadening effects.

In another example, a band structure characteristic is a defect identified by analysis of an optical dispersion metric.

FIG. 4 illustrates the imaginary portion, $\in_2$, of the complex dielectric constant, k, of an exemplary high-k material, $SiO_xHfO_2SiN_5$, obtained from ellipsometry data using Off-Line Spectral Analysis (OLSA) software available from KLA-Tencor Corporation (Milpitas, Calif.). Optical measurements using an ellipsometer or a reflectometer are effective for measuring energy band structures in the 1.3-3 eV range, as illustrated in FIG. 4. In contrast, X-ray photoelectron spectroscopy (XPS) measurements are limited to measurement of band gap at energy levels greater than five electron volts.

Dispersion curve 130 illustrates defect modes and absorption lines associated with the $SiO_xHfO_2SiN_5$ film. By way of example, defects can be identified based on the curve 121 in a number of different ways.

In some examples, a defect is identified if the magnitude of the dispersion metric exceeds a threshold value at any point within a selected spectral range. In some examples, the selected spectral range is below the band gap of measured film. For example, as illustrated in FIG. 4, there are three instances when the magnitude of $\in_2$ exceeds a value of 0.01 within the spectral range of 1.3-3 electron volts (well below the band gap of the $SiO_xHfO_2SiN_5$ film). These include defects 131 and 132 identified in FIG. 4.

In some examples, a defect is identified if the full width, half maximum (FWHM) value of the dispersion metric exceeds a threshold value at any point within a selected spectral range. In some examples, the spectral location of a peak or defect region is used to identify a defect. For example, it may be known that a particular defect always manifests itself as a peak at a particular spectral energy level. In this case, a peak at that energy level may be identified with that particular defect. In some examples, the area under the peak or defect region is used to identify a defect. In some examples, the number of absorption peaks within a selected spectral range is used to identify a defect.

The aforementioned examples are provided for illustration purposes and do not limit the type of band structure characteristics that may be contemplated. Many other band structure characteristics that correlate with the electrical properties, and thus act as effective indicators of the electrical performance of a finished wafer, may be contemplated.

Figure 6:
FIG. 6 is a table illustrative of values for film thickness and two band structure characteristics at different locations of an unfinished semiconductor wafer determined using methods and systems as described herein.

In step 204, an estimate of an electrical performance of a finished multi-layer semiconductor wafer is determined based at least in part on the band structure characteristic identified in step 203 at an early stage of the manufacturing process. As illustrated in FIG. 6, table 300 includes values for film thickness and two band structure characteristics (defect peak value and defect width) at different locations of an unfinished semiconductor wafer determined using the methods and systems discussed herein. As illustrated, the film thickness, defect peak value, and defect width are identified in five different locations of the wafer. In this example, an estimate of the electrical performance (e.g., current density) of the finished wafer at each location is determined based on the linear model of equation (1). In this example, the electrical performance is a function of film thickness (T), defect peak ($D_{peak}$), and defect width ($D_{width}$)

$$\text{Perf}_{electrical} = 8.0351 - 1.2729*T + 36.9009*D_{peak} - 10.2542*D_{width} \quad (1)$$

Figure 7:
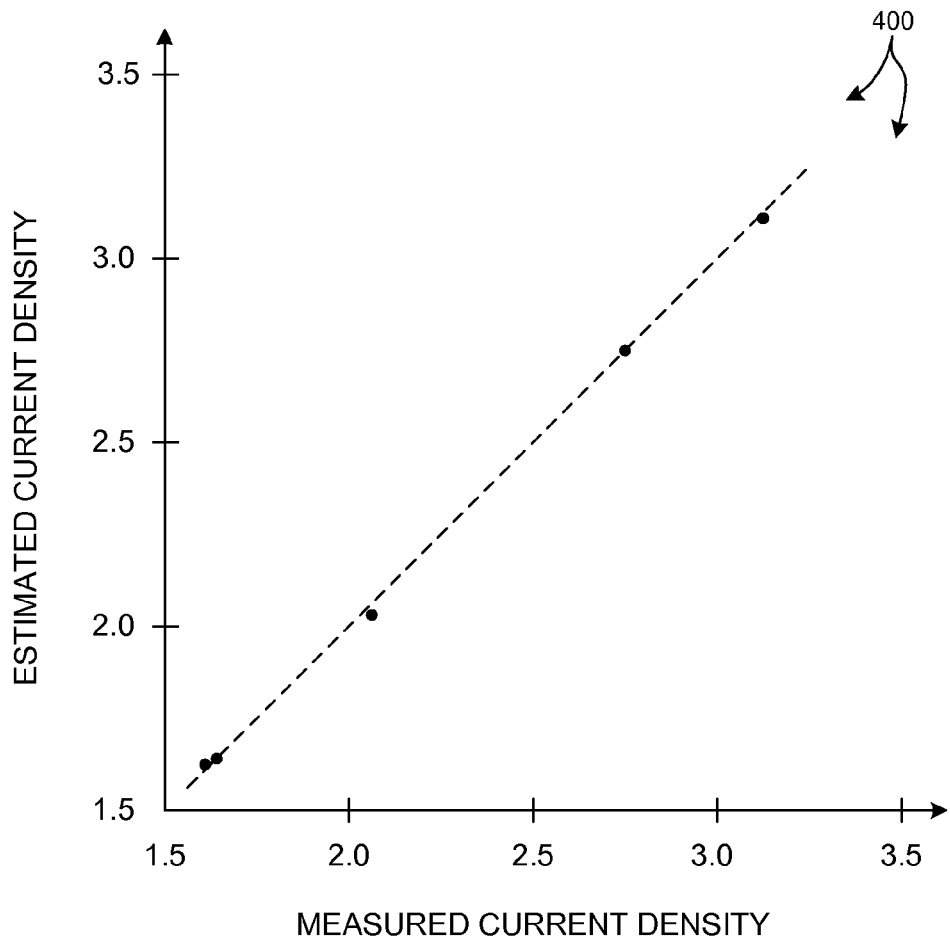
FIG. 7 is a plot illustrative of comparing the estimated current density and the measured current density of the finished wafer at different locations.

FIG. 7 illustrates a plot 400 comparing the current density estimated using the model of equation (1) and the measured current density of the finished wafer at these locations. In this example, the actual electrical performance of the finished wafer is estimated by the linear model of equation (1) with a coefficient of determination ($R^2$) of 0.99.

The model of equation (1) is provided by way of non-limiting example. Many other models (e.g., nonlinear, exponential, etc.) may be identified to accurately relate band structure characteristics identified early in the manufacturing process to electrical performance of finished wafers. Model parameters are resolved based on identified band structure characteristics and the corresponding measured electrical performance of finished wafers. Once the model parameters have been calculated, the model is used to estimate electrical performance of finished wafers based on band structure characteristics identified early in the manufacturing process. Models incorporating any combination of band structure characteristics may be contemplated. Current density is presented herein as an exemplary electrical performance metric, however, any other electrical performance metric useful to characterize finished wafers may be contemplated.

In one further aspect, separate determinations of optical dispersion metrics and band structure characteristics associated with different layers of a wafer can be made based on the same spectral response data. For example, a wafer under measurement may include a semiconductor substrate 112, an intermediate layer 114B, a high-k insulative layer 114A, and an additional film layer (not shown). The spectral response data received from spectrometer 104 includes contributions from all of these layers. A stack layer model that captures the contributions of each of these layers can be used to separately determine optical dispersion metrics and band structure characteristics associated with each different physical layer or group of physical layers under analysis.

In another further aspect, the stack model includes a model of the intrinsic absorption peaks of the semiconductor substrate 112 (e.g., silicon). In one example, the intrinsic absorption peaks are accounted for in the spectral measurement of the high-k film. In this manner, the absorption peaks of the semiconductor substrate may be effectively removed from the spectral response of the high-k film. By isolating the spectral response of the high-k film from the semiconductor substrate, a more accurate determination of defects and band structure characteristics associated with the high-k film layer is achieved.

In another further aspect, band structure characteristics (e.g., band gap and defects) are used to grade wafers and microchips early in the production process based on the quality of the gate insulator. This may avoid the need to grade wafers and microchips at the end of the production process using expensive and time consuming electrical test equipment.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for characterizing thin films of another specimen such as a reticle, which may also be commonly referred to as a mask or a photomask. Many different types of reticles are known in the art, and the terms "reticle," "mask," and "photomask" as used herein are intended to encompass all types of reticles known in the art.

The embodiments described herein generally relate to methods for determining band structure characteristics of multi-layer thin films based on optical dispersion metrics at high throughput. For example, one embodiment relates to a computer-implemented method for determining band structure characteristics of multi-layer thin films based on optical dispersion metrics derived from spectroscopic ellipsometer data. However, the methods described herein are not limited in the types of inspection systems from which optical dispersion metrics may be derived. For example, in one embodiment, the inspection system includes a reflectometer for thin film inspection of the wafer.

In addition, the inspection system may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the determination of band structure characteristics of multi-layer thin films based on optical dispersion metrics at high throughput.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   receiving a spectral response of an unfinished, multi-layer semiconductor wafer across a first spectral range;
   determining an optical dispersion metric of a first layer of the multi-layer semiconductor wafer based at least in part on the spectral response by one or more computing systems;
   determining a band structure characteristic indicative of an electrical performance of the first layer of the multi-layer semiconductor wafer based at least in part on the dispersion metric of the multi-layer semiconductor wafer across a second spectral range within the first spectral range by the one or more computing systems; and
   determining an estimate of the electrical performance of the multi-layer semiconductor wafer based at least in part on the band structure characteristic by the one or more computing systems.

2. The method of claim 1, wherein the first layer is an electrically insulative layer disposed above a semiconductor substrate.

3. The method of claim 2, wherein the first layer includes an intermediate layer between the semiconductor substrate and the electrically insulative layer.

4. The method of claim 1, wherein the band structure characteristic is an interpolated band gap of the first layer and the determining of the interpolated band gap involves curve fitting and interpolation of the optical dispersion metric.

5. The method of claim 1, wherein the band structure characteristic is a band edge of the first layer and the determining of the band edge involves determining that the optical dispersion metric exceeds a threshold value.

6. The method of claim 1, wherein the band structure characteristic is a band broadening associated with the first layer and the determining of the band broadening involves determining an interpolated band gap and a band edge of the first layer and determining a difference between the band edge and the interpolated band gap.

7. The method of claim 1, wherein the band structure characteristic is a defect and the determining of the defect involves determining whether the optical dispersion metric exceeds a threshold value over a spectral range below a band gap of the first layer.

8. The method of claim 1, further comprising:
determining the spectral response of the unfinished, multi-layer semiconductor wafer based on a measurement of the multi-layer semiconductor wafer with either an ellipsometer or a reflectometer.

9. The method of claim 1, further comprising:
determining an optical dispersion property of a second layer of the multi-layer semiconductor wafer based at least in part on the spectral response by the one or more computing systems; and
determining a band structure characteristic indicative of an electrical performance of the second layer of the multi-layer semiconductor wafer based at least in part on the dispersion property of the second layer by the one or more computing systems.

10. A non-transitory, computer-readable medium, comprising:
code for causing a computer to receive a spectral response of an unfinished, multi-layer semiconductor wafer across a first spectral range;
code for causing the computer to determine an optical dispersion metric of a first layer of the multi-layer semiconductor wafer based at least in part on the spectral response;
code for causing the computer to determine a band structure characteristic indicative of an electrical performance of the first layer of the multi-layer semiconductor wafer based at least in part on the dispersion metric of the multi-layer semiconductor wafer across a second spectral range within the first spectral range; and
code for causing the computer to determine an estimate of the electrical performance of the multi-layer semiconductor wafer based at least in part on the band structure characteristic.

11. The non-transitory, computer-readable medium of claim 10, wherein the band structure characteristic is an interpolated band gap of the first layer and the determining of the interpolated band gap involves curve fitting and interpolation of the optical dispersion metric.

12. The non-transitory, computer-readable medium of claim 10, wherein the band structure characteristic is a band edge of the first layer and the determining of the band edge involves determining that the optical dispersion metric exceeds a threshold value.

13. The non-transitory, computer-readable medium of claim 10, wherein the band structure characteristic is a band broadening associated with the first layer and the determining of the band broadening involves determining an interpolated band gap and a band edge of the first layer and determining a difference between the band edge and the interpolated band gap.

14. The non-transitory, computer-readable medium of claim 10, wherein the band structure characteristic is a defect and the determining of the defect involves determining whether the optical dispersion metric exceeds a threshold value over a spectral range below a band gap of the first layer.

15. The non-transitory, computer-readable medium of claim 10, further comprising:
code for causing the computer to determine an optical dispersion property of a second layer of the multi-layer semiconductor wafer based at least in part on the spectral response; and
code for causing the computer to determine a band structure characteristic indicative of an electrical performance of the second layer of the multi-layer semiconductor wafer based at least in part on the dispersion property of the second layer.

16. A system comprising:
an illuminator;
a spectrometer; and
one or more computer systems configured to:
receive a spectral response of an unfinished, multi-layer semiconductor wafer across a first spectral range;
determine an optical dispersion metric of a first layer of the multi-layer semiconductor wafer based at least in part on the spectral response;
determine a band structure characteristic indicative of an electrical performance of the first layer of the multi-layer semiconductor wafer based at least in part on the dispersion metric of the multi-layer semiconductor wafer across a second spectral range within the first spectral range; and
determine an estimate of the electrical performance of the multi-layer semiconductor wafer based at least in part on the band structure characteristic.

17. The system of claim 16, wherein the band structure characteristic is an interpolated band gap of the first layer and the interpolated band gap is determined at least in part by curve fitting and interpolation of the optical dispersion metric.

18. The system of claim 16, wherein the band structure characteristic is a band edge of the first layer and the band edge is determined at least in part by determining that the optical dispersion metric exceeds a threshold value.

19. The system of claim 16, wherein the band structure characteristic is a band broadening associated with the first layer and the band broadening is determined at least in part by determining an interpolated band gap and a band edge of the first layer and determining a difference between the band edge and the interpolated band gap.

20. The system of claim 16, wherein the band structure characteristic is a defect and the defect is determined at least in part by determining whether the optical dispersion metric exceeds a threshold value over a spectral range below a band gap of the first layer.

21. The system of claim 16, wherein the one or more computer systems is further configured to:
determine an optical dispersion property of a second layer of the multi-layer semiconductor wafer based at least in part on the spectral response; and
determine a band structure characteristic indicative of an electrical performance of the second layer of the multi-layer semiconductor wafer based at least in part on the dispersion property of the second layer.

* * * * *